United States Patent
Stinson (10) Patent No.: US 7,127,789 B2
(45) Date of Patent: Oct. 31, 2006

(54) METHOD OF MANUFACTURING A STENT DELIVERY SYSTEM

(75) Inventor: Jonathan S. Stinson, Plymouth, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/790,607

(22) Filed: Mar. 1, 2004

(65) Prior Publication Data
US 2004/0167604 A1    Aug. 26, 2004

Related U.S. Application Data

(63) Continuation of application No. 09/767,212, filed on Jan. 22, 2001, now Pat. No. 6,699,274.

(51) Int. Cl.
*A61M 25/00* (2006.01)
*A61F 2/06* (2006.01)
*B21D 39/00* (2006.01)

(52) U.S. Cl. ............... 29/434; 29/517; 29/525.13; 623/1.12; 606/108

(58) Field of Classification Search .......... 29/434, 29/517, 520, 525.13, 525.14; 623/1.12; 606/108
See application file for complete search history.

(56) References Cited

U.S. PATENT DOCUMENTS

| | | | |
|---|---|---|---|
| 4,732,152 A | 3/1988 | Wallstén et al. |
| 4,990,151 A | 2/1991 | Wallstén |
| 5,026,377 A | 6/1991 | Burton et al. |
| 5,061,275 A | 10/1991 | Wallstén et al. |
| 5,234,457 A | 8/1993 | Andersen |
| 5,366,504 A | 11/1994 | Andersen et al. |
| 5,405,378 A | 4/1995 | Strecker |
| 5,484,444 A | 1/1996 | Braunschweiler et al. |
| 5,690,644 A | 11/1997 | Yurek et al. |
| 5,709,703 A | 1/1998 | Lukic et al. |
| 5,792,144 A | 8/1998 | Fischell et al. |
| 5,843,161 A * | 12/1998 | Solovay ............... 623/1.13 |
| 5,876,445 A | 3/1999 | Andersen et al. |
| 5,957,974 A | 9/1999 | Thompson et al. |

(Continued)

FOREIGN PATENT DOCUMENTS

CA    2356754 A1    7/2000

(Continued)

OTHER PUBLICATIONS

Watkinson et al., 'The Role of Self-Expanding Metallic Endoprostheses in Esophageal Strictures,' Seminars in Interventional Radiology, 13 (1) :17-26 (1996).

(Continued)

*Primary Examiner*—Jermie E. Cozart
(74) *Attorney, Agent, or Firm*—Kriegsman & Kriegsman (57) ABSTRACT

In one embodiment, the stent delivery system comprises an inner catheter. A handle is disposed at the proximal end of the inner catheter, and an enlarged tip is disposed at the distal end thereof. A stent engaging sleeve coaxially surrounds and is secured to a portion of the inner catheter proximally contiguous to the tip. A stent is mounted over the stent engaging sleeve in a longitudinally stretched state and is maintained, until deployment, in the stretched state by a stent restraining sleeve. The stent restraining sleeve, which coaxially surrounds the stent and is appropriately sized to maintain the stent in its stretched state, is a braided tube formed directly over the stent. The system also includes an outer catheter that surrounds much of the distal end of the inner catheter up to its tip, the outer catheter being adapted for axial movement relative to the inner catheter.

9 Claims, 6 Drawing Sheets

U.S. PATENT DOCUMENTS

| | | |
|---|---|---|
| 5,976,155 A | 11/1999 | Foreman et al. |
| 6,004,328 A | 12/1999 | Solar |
| 6,152,944 A | 11/2000 | Holman et al. |
| 6,254,609 B1 | 7/2001 | Vrba et al. |

FOREIGN PATENT DOCUMENTS

| | | |
|---|---|---|
| CA | 2360620 A1 | 8/2000 |
| CA | 2367209 A1 | 10/2000 |
| EP | 0553960 A1 | 8/1993 |
| EP | 0 775 470 A1 | 5/1997 |
| EP | 0775470 A1 | 5/1997 |
| EP | 0788802 A2 | 8/1997 |
| EP | 1053722 A2 | 11/2000 |
| FR | 2753907 | 4/1998 |
| WO | WO 96/32078 | 10/1996 |
| WO | WO 00/41525 | 7/2000 |
| WO | WO 00/41525 A2 | 7/2000 |

OTHER PUBLICATIONS

Strecker et al., 'Nitinol Esophageal Stents: New Designs and Clinical Indications,' Cardiovasc. Intervent. Radiol., 19:15-20 (1996).

ULTRAFLEX (TM) Esophageal Stent System, Boston Scientific Corporation, Watertown, MA (1994).

Covered Ultraflex (TM) Esophageal Stent System, Boston Scientific Corporation, Natick, MA, published before the filing of the present application.

Copy of International Search Report dated Sep. 19, 2002, from corresponding PCT Application No. PCT/EP02/00611.

* cited by examiner

METHOD OF MANUFACTURING A STENT DELIVERY SYSTEM

CROSS-REFERENCE TO RELATED APPLICATIONS

The present application is a continuation of U.S. patent application Ser. No. 09/767,212, filed Jan. 22, 2001 now U.S. Pat. No. 6,699,274 B2, the disclosure of which is incorporated herein by reference.

BACKGROUND OF THE INVENTION

The present invention relates generally to medical stents (hereinafter "stents") and relates more particularly to stent delivery systems.

A stent is a tubular endoprosthesis placed within a body lumen to maintain its patency. For example, a stent may be used to maintain the patency of an esophagus or other passageway occluded by a tumor or of a blood vessel constricted by plaque. Most stents fall into one of the following two classes: (i) balloon-expandable stents; and (ii) self-expandable stents. Generally speaking, a stent delivery system includes the stent and some means for positioning and fixing the stent in place within a body lumen.

A balloon-expandable stent is typically a ductile metal tube. The delivery system for such a stent typically includes an inflatable balloon secured to the distal end of a catheter, the balloon-expandable stent being secured to the catheter over the inflatable balloon. In use, the catheter is introduced to a desired site within a body lumen, and the balloon is expanded until the stent positioned thereover is inelastically expanded to its desired size against the walls of the lumen. The balloon is then deflated, and the catheter is withdrawn from the site, thereby leaving the expanded stent in place against the walls of the lumen. An example of a balloon-expandable stent and delivery system therefor is disclosed in U.S. Pat. No. 4,922,905, inventor Strecker, issued May 1990, the disclosure of which is incorporated herein by reference.

A self-expandable stent is typically an elastic tube that self-expands after having been compacted. Illustrative examples of self-expandable stents are disclosed in the following documents, all of which are incorporated herein by reference: U.S. Pat. No. 5,876,445, inventors Andersen et al., issued Mar. 2, 1999; U.S. Pat. No. 5,366,504, inventors Andersen et al., issued Nov. 22, 1994; U.S. Pat. No. 5,234,457, inventor Andersen, issued Aug. 10, 1993; U.S. Pat. No. 5,061,275, inventors Wallstén et al., issued Oct. 29, 1991; Watkinson et al., "The Role of Self-Expanding Metallic Endoprostheses in Esophageal Strictures," *Seminars in Interventional Radiology,* 13(1): 17–26 (March 1996); and Strecker et al., "Nitinol Esophageal Stents: New Designs and Clinical Indications," *Cadiovasc. Intervent. Radiol.,* 19:15–20 (1996).

The delivery system for a self-expandable stent typically comprises a catheter and a restraint for temporarily holding the stent in a compressed state at the distal end of the catheter. In use, the catheter is introduced to a desired site within a body lumen, and the restraint is removed, thereby allowing the stent to expand by its own elastic restoring force against the walls of the lumen. One of the more common self-expandable stent delivery systems of the above-described type comprises a coaxial tube assembly. More specifically, said delivery system comprises an inner catheter and an outer catheter, said outer catheter being coaxial with said inner catheter. The inner and outer catheters are appropriately sized so that a stent inserted over the distal end of the inner catheter is maintained in a compressed state by the inner surface of the outer catheter. In use, the assembly is introduced to a desired site, and the outer catheter is axially retracted relative to the inner catheter, thereby allowing the stent to self-expand off the inner catheter and against the walls of the lumen.

Illustrative examples of the aforementioned type of delivery system include the following U.S. patents, all of which are incorporated herein by reference: U.S. Pat. No. 5,484,444, inventors Braunschweiler et al., issued Jan. 16, 1996; U.S. Pat. No. 5,026,377, inventors Burton et al., issued Jun. 25, 1991; U.S. Pat. No. 4,990,151, inventor Wallstén, issued Feb. 5, 1991; and U.S. Pat. No. 4,732,152, inventors Wallstén et al., issued Mar. 22, 1988. A commercial embodiment of the above-described delivery system is the UNISTEP PLUS™ delivery system (Boston Scientific Corporation, Natick, Mass.).

Although the above-described coaxial tube delivery system is well-suited for many types of self-expandable stents, such a delivery system is not particularly well-suited for those self-expandable stents that have limited axial strength, such as the Strecker stent—a knitted nitinol wire stent disclosed in U.S. Pat. No 5,366,504 and commercially available from Boston Scientific Corporation, Natick, Mass. This is because such stents are often unable to resist becoming axially compressed during assembly of the coaxial tube delivery system, when the distal end of the outer catheter must be drawn across the stent, and/or during deployment of the coaxial tube delivery system, when the distal end of the outer catheter must be withdrawn across the stent.

Consequently, alternative delivery systems have been devised for use with the Strecker stent and with other like stents of limited axial strength. One such system, which is exemplified by the ULTRAFLEX™ esophageal stent system (Boston Scientific Corporation, Natick, Mass.), comprises a stent of the aforementioned type, said stent being mounted on an inner catheter and being encased in a pharmaceutical grade dissolvable gelatin to maintain the stent in a compressed state. An outer catheter surrounds the gelatin-encased stent. In use, the system is inserted into a patient's esophagus and the outer catheter is retracted. Moisture present in the esophagus causes the restraining gelatin to dissolve, thereby allowing the stent to expand.

Another delivery system devised for use with the Strecker stent and like stents of limited axial strength is disclosed in U.S. Pat. No. 5,405,378, inventor Strecker, which issued Apr. 11, 1995, and which is incorporated herein by reference. Said delivery system, which does not include an outer catheter, uses a crocheted suture cord to compress the stent against a catheter core. The crocheted cord is connected to a finger ring at the proximal end of the delivery system. Retraction of the finger ring unravels the cord in a circular manner down the length of the stent, gradually deploying the stent. A commercial embodiment of the aforementioned delivery system is the COVERED ULTRAFLEX™ esophageal stent system (Boston Scientific Corporation, Natick, Mass.).

Unfortunately, the manufacture of the aforementioned crocheted cord delivery system is typically performed manually and can be quite taxing physically as a great deal of strength is required to tightly stretch the stent down on the catheter while crocheting the cord around the stent. Another problem with the foregoing system is that, during deployment, the crocheted cord does not always unravel correctly and completely.

SUMMARY OF THE INVENTION

It is an object of the present invention to provide a novel stent delivery system.

It is another object of the present invention to provide a stent delivery system as described above that overcomes at least some of the above-described shortcomings associated with existing stent delivery systems.

It is still another object of the present invention to provide a stent delivery system that has a minimal number of parts, that can be mass-produced, that is easy to manufacture and that is easy to use.

Therefore, in furtherance of the above and other objects to be described or to become apparent from the description below, there is provided herein a stent delivery system constructed according to the teachings of the present invention, said stent delivery system comprising, in one embodiment, (a) an inner catheter; (b) an outer catheter, said outer catheter surrounding at least a portion of the length of said inner catheter and adapted for axial movement relative to said inner catheter; (c) a self-expandable stent disposed between said inner catheter and said outer catheter; and (d) a stent restraining member disposed between said outer catheter and said self-expandable stent, said stent restraining member being dimensioned to maintain said self-expandable stent in a compressed state.

The aforementioned stent restraining member may be a braided tube (or any other type of tube) surrounding said self-expandable stent, said braided tube preferably being made from a strong, flexible, filamentary material having a low coefficient of friction. Examples of such materials may be a fine polyester or metal wire. The braided tube may be formed directly over the stent, preferably using an automated braiding machine, or may be pre-formed and then inserted over the stent. Where the braided tube is pre-formed and inserted over the stent, the system preferably further includes a braid holding sleeve secured to the inner catheter, said braid holding sleeve being adapted to receive the proximal end of the braided tube. The distal end of the stent restraining member is preferably mechanically coupled to the distal end of the outer catheter so that retraction of the outer catheter causes the stent restraining member to retract from the stent, thereby allowing the stent to self-expand.

Instead of being a tube, the stent restraining member may be a coil helically wrapped around the stent, said coil preferably being made from a strong, flexible, wire-like, thread-like or ribbon-like material having a low coefficient of friction.

The self-expandable stent is preferably a knitted mesh of nitinol wire flexible in both the radial and longitudinal axes, said stent preferably being coaxially positioned relative to the inner catheter and being stretched longitudinally thereacross.

The outer catheter may be a solid tube or may be a tube having a longitudinal split extending proximally from its distal end at least partially along its length. Where the outer catheter has a longitudinal split, said split is preferably sealed after the outer catheter has been advanced over and secured to the stent restraining member.

The stent delivery system preferably further comprises means for deterring said self-expandable stent from sliding proximally relative to said inner catheter during deployment, said deterring means further comprising a stent engaging sleeve fixed to said inner catheter, said self-expandable stent surrounding said stent engaging sleeve, said stent engaging sleeve having an outer surface adapted to engage said self-expandable stent in such a way as to deter said self-expandable stent from sliding proximally relative thereto.

In another embodiment, the stent delivery system of the present invention comprises (a) an inner catheter; (b) an outer catheter, said outer catheter surrounding at least a portion of the length of said inner catheter and adapted for axial movement relative to said inner catheter; and (c) a self-expandable stent disposed between said inner catheter and said outer catheter, said self-expandable stent being flexible in both the radial and longitudinal axes, said self-expandable stent being held in a compressed state by said outer catheter.

The aforementioned self-expandable stent is preferably a knitted mesh of nitinol wire coaxially mounted on said inner catheter. The outer catheter preferably has a longitudinal split extending proximally from its distal end at least partially along its length, said split preferably being sealed after the outer catheter has been advanced over and secured to the stent restraining member.

The stent delivery system preferably further comprises means for deterring said self-expandable stent from sliding proximally relative to said inner catheter during deployment, said deterring means further comprising-a stent engaging sleeve fixed to said inner catheter, said self-expandable stent surrounding said stent engaging sleeve, said stent engaging sleeve having an outer surface adapted to engage said self-expandable stent in such a way as to deter said self-expandable stent from sliding proximally relative thereto.

The present invention is also directed to a method of manufacturing a stent delivery system, said method comprising, in one embodiment, the steps of (a) providing an inner catheter; (b) compressing a self-expandable stent over said inner catheter; (c) while said self-expandable stent is in a compressed state, positioning a braided tube around said inner catheter and said self-expandable stent, said braided tube being dimensioned to maintain said self-expandable stent in said compressed state; and (d) positioning an outer catheter around said braided tube, said outer catheter being adapted for axial movement relative to said inner catheter.

The aforementioned braided tube positioning step may comprise forming a braided tube over said self-expandable stent and said inner catheter or may comprise pre-forming a braided tube and then sliding said pre-formed braided tube over said stent and said inner catheter.

The stent and the inner catheter are preferably coaxially disposed, with said stent being flexible in both the longitudinal and radial axes. The aforementioned compressing step preferably comprises stretching said stent longitudinally across the length of said inner catheter.

Preferably, said method further comprises mechanically coupling said outer catheter to said braided tube for axial movement. The outer catheter may be a solid tube or may be a tube provided with a longitudinal slit extending at least a part of the length thereof In the case of the tube with a longitudinal slit, the method preferably further comprises, after said outer catheter positioning step, the step of sealing said longitudinal slit.

The above method preferably further comprises, before said compressing step, the step of fixing a stent engaging sleeve to said inner catheter, said self-expandable stent surrounding said stent engaging sleeve, said stent engaging sleeve having an outer surface adapted to engage said self-expandable stent in such a way as to deter said self-expandable stent from sliding proximally relative thereto. In addition, said method preferably also comprises, before said outer catheter positioning step, the steps of fixing a braid holding sleeve to said inner catheter and securing the proximal end of said braided tube to said braid holding sleeve.

In another embodiment, the method of the present invention comprises the steps of (a) providing an inner catheter; (b) compressing a self-expandable stent over said inner catheter; (c) while said self-expandable stent is in a compressed state, wrapping a helical restraint around said inner catheter and said self-expandable stent, said helical restraint being dimensioned to maintain said self-expandable stent in said compressed state; and (d) positioning an outer catheter around said helical restraint, said outer catheter being adapted for axial movement relative to said inner catheter.

The aforementioned helical restraint is preferably made from a strong, flexible filamentary or ribbon-like material having a low coefficient of friction. Preferably, said method further comprises mechanically coupling said outer catheter to said braided tube for axial movement. The outer catheter is preferably a tube provided with a longitudinal slit extending at least a part of the length thereof, the method preferably further comprising, after said outer catheter positioning step, the step of sealing said longitudinal slit.

The subject method preferably still further comprises, before said compressing step, the step of fixing a stent engaging sleeve to said inner catheter, said self-expandable stent surrounding said stent engaging sleeve, said stent engaging sleeve having an outer surface adapted to engage said self-expandable stent in such a way as to deter said self-expandable stent from sliding proximally relative thereto.

In still another embodiment, the method of the present invention comprises the steps of (a) providing an inner catheter; (b) compressing a self-expandable stent over said inner catheter, said self-expandable stent being flexible in both the radial and longitudinal axes; and (c) positioning an outer catheter around said self-expandable stent, said outer catheter being adapted for axial movement relative to said inner catheter and being dimensioned to maintain said self-expandable stent in a compressed state.

Preferably, the aforementioned stent is a knitted mesh of nitinol wire. In addition, the outer catheter is preferably provided with a longitudinal slit extending at least a part of the length thereof, said method further comprising, after said outer catheter positioning step, the step of sealing said longitudinal slit.

The subject method preferably further comprises, before said compressing step, the step of fixing a stent engaging sleeve to said inner catheter, said self-expandable stent surrounding said stent engaging sleeve, said stent engaging sleeve having an outer surface adapted to engage said self-expandable stent in such a way as to deter said self-expandable stent from sliding proximally relative thereto.

Additional objects, features,-aspects and advantages of the present invention will be set forth, in part, in the description which follows and, in part, will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate preferred embodiments of the invention and, together with the description, serve to explain the principles of the invention. In the drawings wherein like reference numerals represent like parts.

DETAILED DESCRIPTION OF PREFERRED EMBODIMENTS

Figure 1:
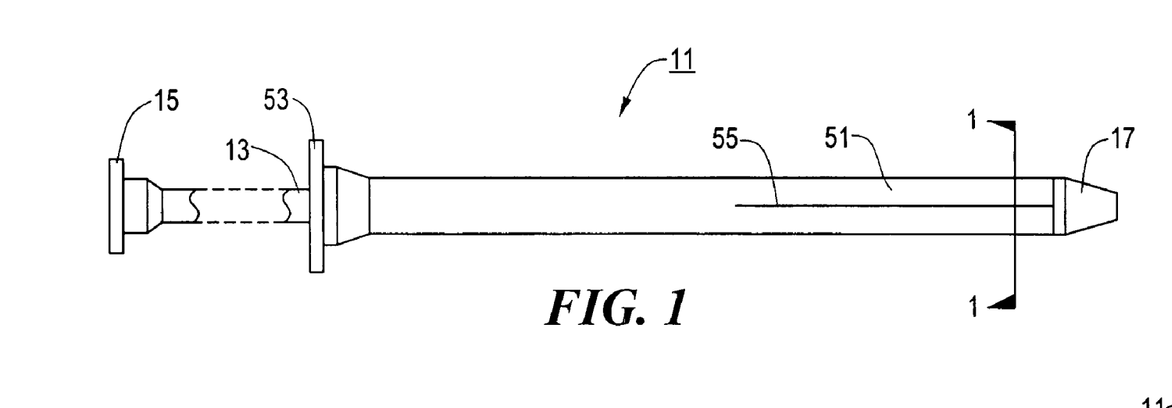
FIG. 1 is a side view of a first embodiment of a stent delivery system constructed according to the teachings of the present invention.
Figure 2:
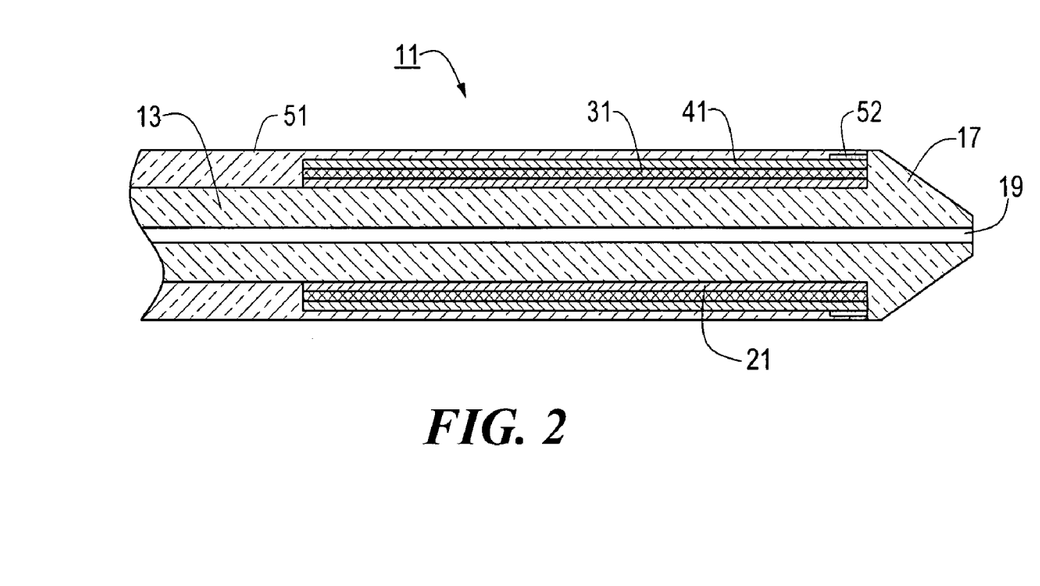
FIG. 2 is a fragmentary schematic longitudinal section view of the stent delivery system of FIG. 1, showing the distal end thereof.
Figure 3:
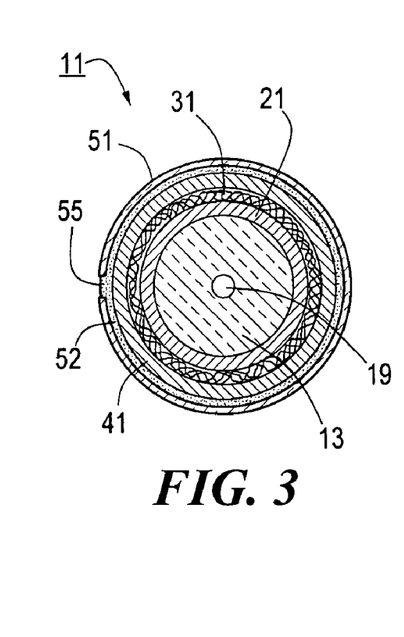
FIG. 3 is a schematic transverse section view of the stent delivery system of FIG. 1 taken along line 1—1.

Referring now to FIGS. 1 through 3, there are shown various views of a first embodiment of a stent delivery system constructed according to the teachings of the present invention, said stent delivery system being represented generally by reference numeral 11.

System 11 comprises a flexible, inner catheter 13. A handle 15 is disposed at the proximal end of catheter 13, and an enlarged tip 17 is disposed at the distal end of catheter 13. A lumen 19 extends longitudinally through catheter 13, lumen 19 being adapted to receive a guide wire for use in positioning system 11 at a desired position within a body lumen.

Figure 4:
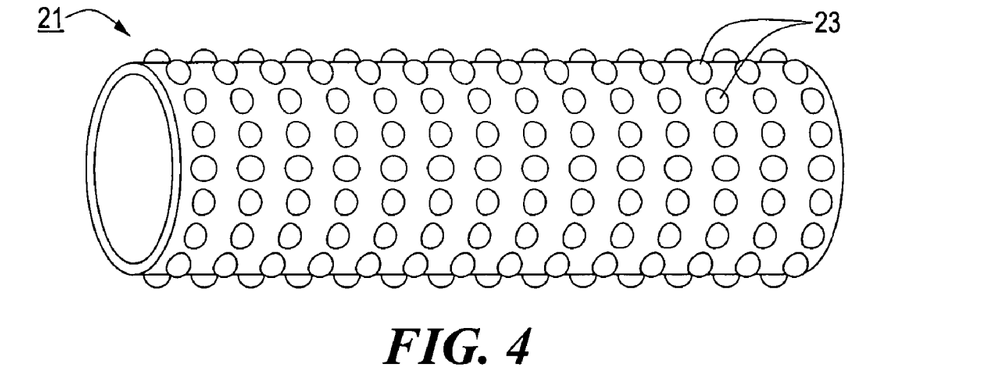
FIG. 4 is an enlarged perspective view of the stent engaging sleeve of the stent delivery system of FIG. 1.

System 11 further comprises a stent engaging sleeve 21, sleeve 21 coaxially surrounding and secured (e.g., by a frictional fit) to that portion of catheter 13 proximally contiguous to tip 17. The primary purpose of sleeve 21 is to engage a stent mounted thereover in such a way as to prevent said stent, during deployment, from sliding proximally relative to catheter 13. To this end, as can be seen in FIG. 4, the outer surface of sleeve 21 is provided with a plurality of projections 23 adapted to engage the mesh-like structure of a stent in such a way as to restrain axial movement of the stent. Although, in the embodiment shown, projections 23 are in the form of bumps, it can readily be appreciated that projections 23 may take a variety of shapes including, but not limited to, ridges, hooks, threads, pegs, etc. Alternatively, sleeve 21 may be provided with a roughened surface, such as that of sandpaper, to increase the coefficient of friction between the stent and sleeve 21 and, thereby, to restrain axial movement of the stent during deployment. In still another alternative embodiment, sleeve 21 may be made of a soft, compressible material, such as silicone, so that a stent mounted thereover becomes partially embedded therein and cannot easily slide proximally relative thereto during deployment.

Figure 5:
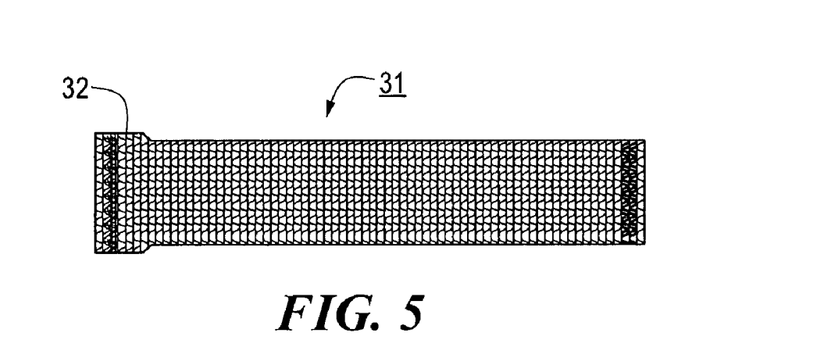
FIG. 5 is a side view of the stent of the stent delivery system of FIG. 1, the stent being shown in a relaxed, expanded state.

Referring back to FIGS. 2 and 3, system 11 additionally comprises a self-expandable stent 31 (shown separately in FIG. 5). Although, in the present embodiment, stent 31 is a self-expandable stent of the type comprising a knitted mesh of nitinol (a nickel/titanium alloy) wire flexible in both the radial and longitudinal axes, stent 31 is not so limited and may be virtually any type of self-expandable stent. A preferred example of stent 31 is the ULTRAFLEX™ Strecker esophageal stent—a self-expandable stent comprising a knitted mesh of 0.15 inch nitinol wire flexible in both the radial and longitudinal axes. Said ULTRAFLEX™ Strecker esophageal stent has a length of 7 cm, 10 cm or 15 cm and an expanded diameter of 18 mm, the proximal end of the stent forming a 5 mm collar 32 having an expanded diameter of 20 mm.

Stent 31 is mounted over sleeve 21 in a stretched or compressed state and is maintained, until deployment, in said stretched or compressed state in the manner to be described below.

Figure 6:
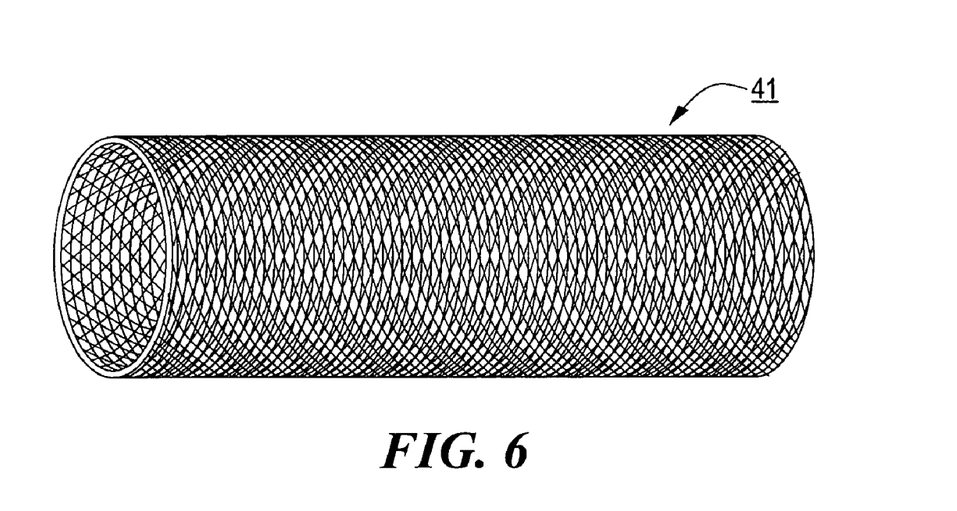
FIG. 6 is an enlarged perspective view of the stent restraining sleeve of the stent delivery system of FIG. 1.

System 11 further comprises a stent restraining sleeve 41 (shown separately in FIG. 6). Sleeve 41 coaxially surrounds stent 31 and is appropriately sized to maintain stent 31 in its stretched state. In the present embodiment, sleeve 41 is a braided tube, said braided tube preferably being made from a wire or filament that is strong, flexible and has a low coefficient of friction. Said wire or filament may be made of a fine polyester, metal or like material.

Figure 7:
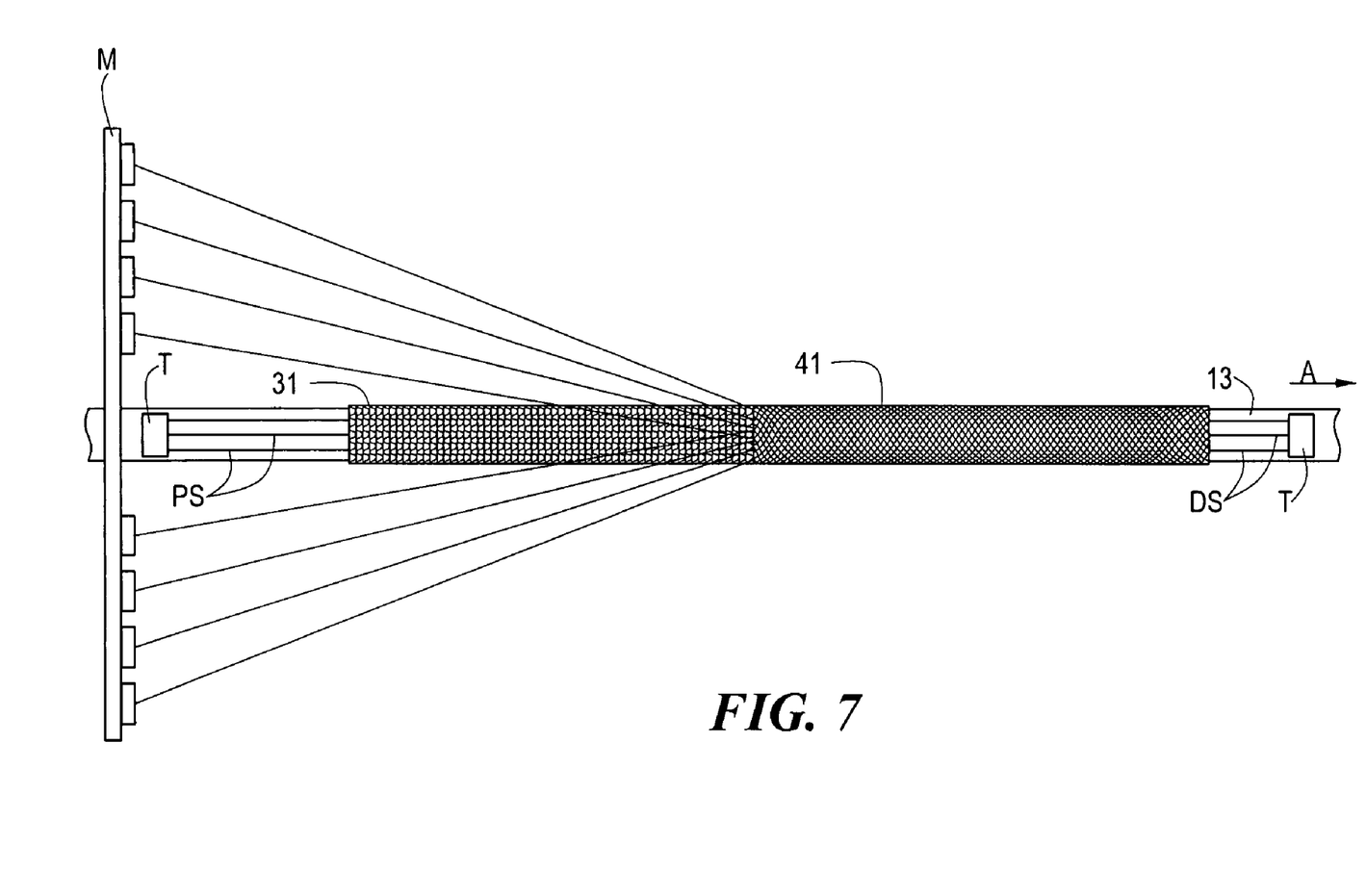
FIG. 7 is a schematic fragmentary side view illustrating the manner in which the stent restraining sleeve of the stent delivery system of FIG. 1 may be formed over the stent thereof by a rolling braid technique.

In the present embodiment, sleeve 41 is formed directly over stent 31 in the following manner: First, as shown in FIG. 7, stent 31 is stretched tightly over sleeve 21 and catheter 13. This may be done by looping or hooking proximal and distal strings PS and DS, respectively, onto the proximal and distal ends, respectively, of stent 31 and then by tightly pulling proximal strings PS proximally and distal strings DS distally, either manually or using a motorized pulling mechanism, until stent 31 is fully stretched. In its stretched state, stent 31 may have a diameter of about 5–6 mm, as compared to a diameter of 18–20 mm in its expanded or un-stretched state. Adhesive tape T or the like is then used to secure proximal strings PS and distal strings DS to catheter 13 in their pulled-apart states to maintain stent 31 in its stretched configuration.

Next, the above-described assembly is then passed through a wire braiding machine M in the direction indicated by arrow A, which forms sleeve 41 directly over stent 31. Machine M may be a conventional wire braiding machine, such as Model 40/98 from Rotek Technologies, Inc. (Ormond Beach, Fla.), which is capable of braiding twenty wires or filaments. After sleeve 41 has been formed, strings PS and DS and tape T are removed, leaving sleeve 41 to restrain stent 31 in its stretched state.

Figures 8, 9:
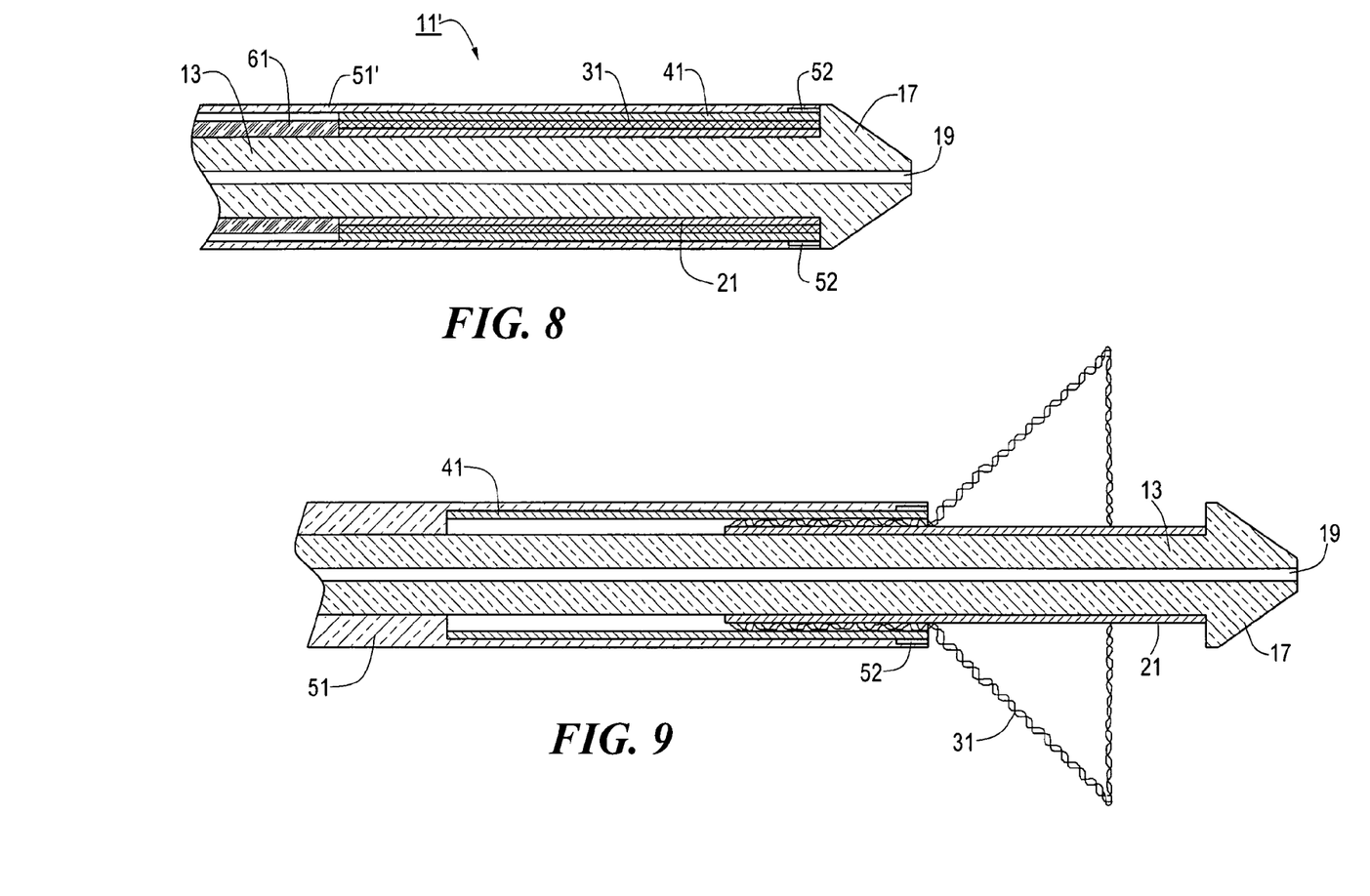
FIG. 8 is a fragmentary schematic longitudinal section view of a second embodiment of a stent delivery system constructed according to the teachings of the present invention.
FIG. 9 is a schematic fragmentary longitudinal section view of the distal end of the stent delivery system of FIG. 1, illustrating the system during stent deployment.

Referring back now to FIGS. 1 through 3, system 11 also comprises a flexible, outer catheter 51, catheter 51 coaxially surrounding much of the distal end of catheter 13 up to tip 17. Catheter 51 is adapted for axial movement relative to catheter 13, and a handle 53 is disposed at the proximal end of catheter 51 for use in axially moving catheter 51 relative to catheter 13. In order to accommodate sleeve 41, stent 31 and sleeve 21 between catheter 51 and catheter 13, the distal end of catheter 51 is provided with an increased inside diameter. Alternatively, instead of constructing catheter 51 to have an increased inside diameter at its distal end, there is shown in FIG. 8 a system 11' comprising an outer catheter 51' of constant inside diameter, system 11' further comprising a space-filling jacket 61 secured (e.g., by a friction-fit) to catheter 13 proximally relative to sleeve 21. Jacket 61 serves to prevent proximal sliding of stent 31 and sleeve 21 during deployment and also serves to prevent buckling and/or kinking of catheter 51' during deployment.

Referring back to FIGS. 2 and 3, the distal end of catheter 51 is secured to the distal end of sleeve 41 by an adhesive 52 so that sleeve 41 is mechanically coupled to catheter 51 for purposes of axial movement. (Instead of using adhesive 52, catheter 51 and sleeve 41 may be coupled together using other mechanical means, such as a clamp, a cable-tie, pins or a crimp.) Due to the coupling together of catheter 51 and sleeve 41, retraction (i.e., proximal movement) of catheter 51 relative to catheter 13 simultaneously results in the retraction of sleeve 41 relative to stent 31.

To facilitate the advancement of catheter 51 over sleeve 41 during the assembly of system 11, catheter 51 is provided with a longitudinal split 55 extending proximally from its distal end. The reason for providing split 55 in catheter 51 is to avoid having to slide catheter 51 past sleeve 41 and possibly dislodging sleeve 41 from stent 31. In the present embodiment, split 55 extends proximally only partially from the distal end of catheter 51; however, it can readily be appreciated that split 55 could extend the entire length of catheter 51. After catheter 51 has been properly positioned over sleeve 41, adhesive 52 is used to bond the distal ends of catheter 51 and sleeve 41, as described above, and is also used to seal split 55. As can readily be appreciated, instead of sealing split 55 with adhesive 52, split 55 could be welded together.

In use, system 11 is inserted into a body lumen and advanced to a desired site therewithin in the conventional fashion. System 11 is then deployed by retracting (i.e., sliding proximally) catheter 51 relative to catheter 13. As seen in FIG. 9, as catheter 51 is retracted, sleeve 41 slides off stent 31, thereby permitting stent 31 to self-expand. Sleeve 21 helps to ensure that stent 31 does not retract with sleeve 41 and catheter 51.

Figure 10:
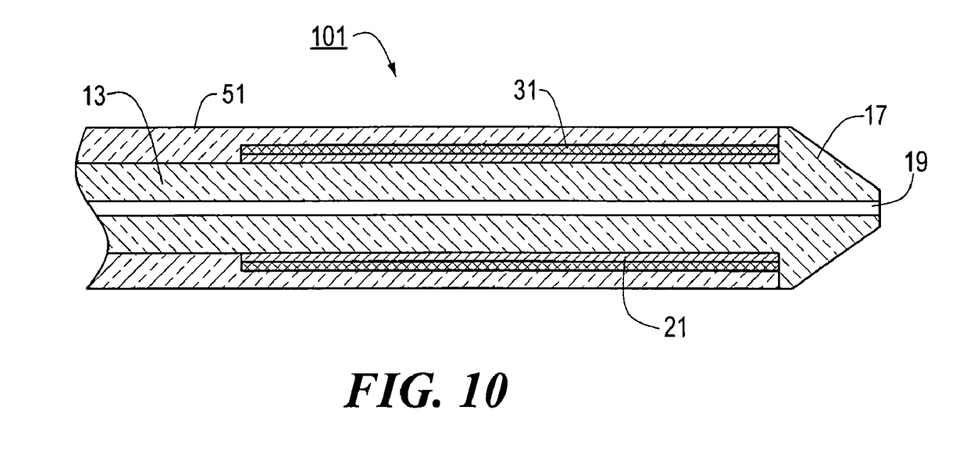
FIG. 10 is a schematic fragmentary longitudinal section view of a third embodiment of a stent delivery system constructed according to the teachings of the present invention.
Figure 11:
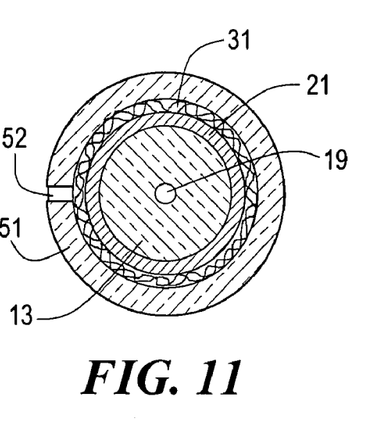
FIG. 11 is a schematic transverse section view of the stent delivery system of FIG. 10.

Referring now to FIGS. 10 and 11, there are shown longitudinal and transverse section views, respectively, of a third embodiment of a stent delivery system constructed according to the teachings of the present invention, said stent delivery system being represented generally by reference numeral 101.

System 101 is similar in most respects to system 11, the principal difference between the two systems being that system 101 does not include sleeve 41 of system 11. Instead, system 101 relies on catheter 51 to function as the external restraint mechanism for keeping stent 31 in its compressed state until deployment. A lubricant (not shown) may be applied to the inside surface of catheter 51 to ensure that stent 31 does not axially compress, during deployment, as catheter 51 is moved proximally. As can readily be appreciated, catheter 51 of system 101 could be replaced with catheter 51' and jacket 61.

System 101 is used in the same manner as system 11.

Figure 12:
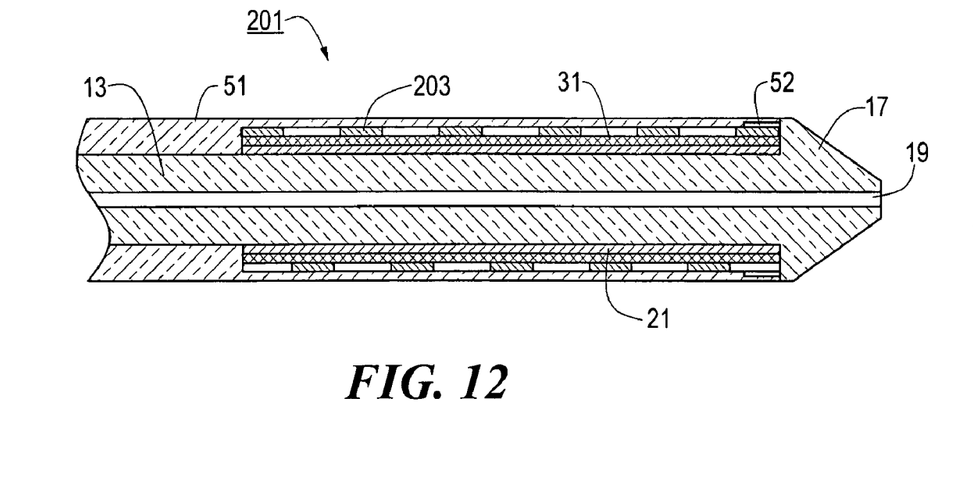
FIG. 12 is schematic fragmentary longitudinal section view of a fourth embodiment of a stent delivery system constructed according to the teachings of the present invention.
Figure 13:
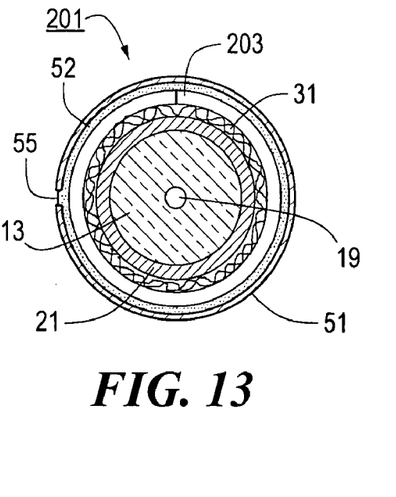
FIG. 13 is a schematic transverse section view of the stent delivery system of FIG. 12.

Referring now to FIGS. 12 and 13, there are shown longitudinal and transverse section views, respectively, of a fourth embodiment of a stent delivery system constructed according to the teachings of the present invention, said stent delivery system being represented generally by reference numeral 201.

System 201 is similar in most respects to system 11, the principal difference between the two systems being that system 201 comprises, instead of sleeve 41, a stent restraining element in the form of a single helical coil 203 wrapped around stent 31. Coil 203 may be made of wire, thread, ribbon or like materials and may be wrapped around stent 31 either manually or with the use of an automated winding machine. The distal end of coil 203 is coupled to the distal end of catheter 51. One advantage to using coil 203, instead of sleeve 41, is that it is less complicated and less costly, particularly in terms of automated equipment, to apply a single, coiled containment element than it is to apply multiple elements in the form of a braid. As can readily be appreciated, catheter 51 of system 201 could be replaced with catheter 51' and jacket 61.

System 201 is used in the same manner as system 11.

Figure 14:
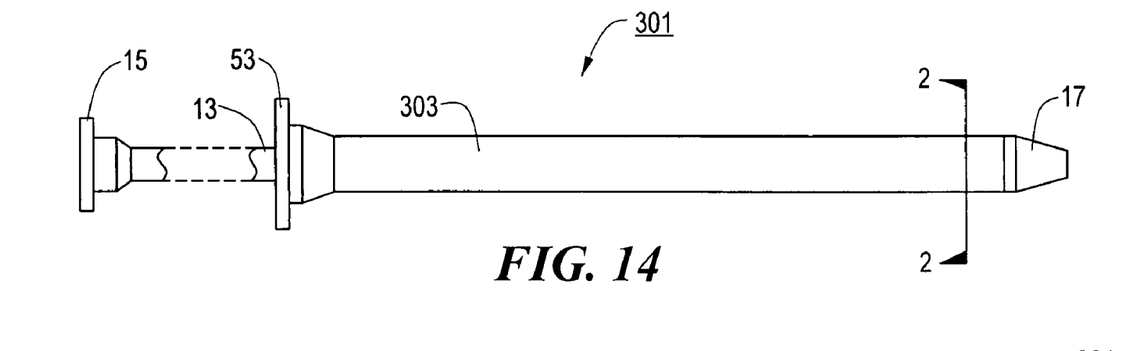
FIG. 14 is a side view of a fifth embodiment of a stent delivery system constructed according to the teachings of the present invention.
Figure 15:
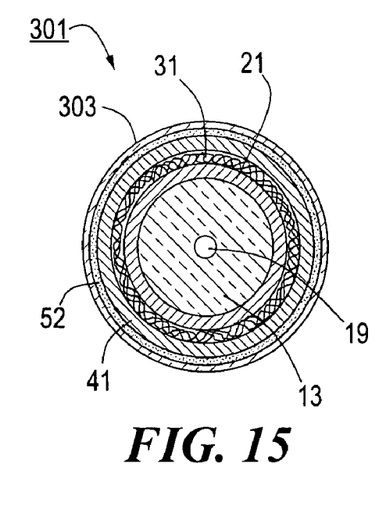
FIG. 15 is a schematic transverse section view of the stent delivery system of FIG. 14 taken along line 2—2.

Referring now to FIGS. 14 and 15, there are shown side and transverse section views, respectively, of a fifth embodiment of a stent delivery system constructed according to the teachings of the present invention, said stent delivery system being represented generally by reference numeral 301.

System 301 is similar in most respects to system 11, the principal difference between the two systems being that system 301 includes a flexible outer catheter 303 that is identical to catheter 51, except that catheter 303 is not fabricated with a longitudinal split. The distal end of catheter 303 is mechanically coupled to the distal end of sleeve 41. As can readily be appreciated, catheter 51 of system 301 could be replaced with catheter 51' and jacket 61.

System 301 is used in the same manner as system 11.

Figure 16:
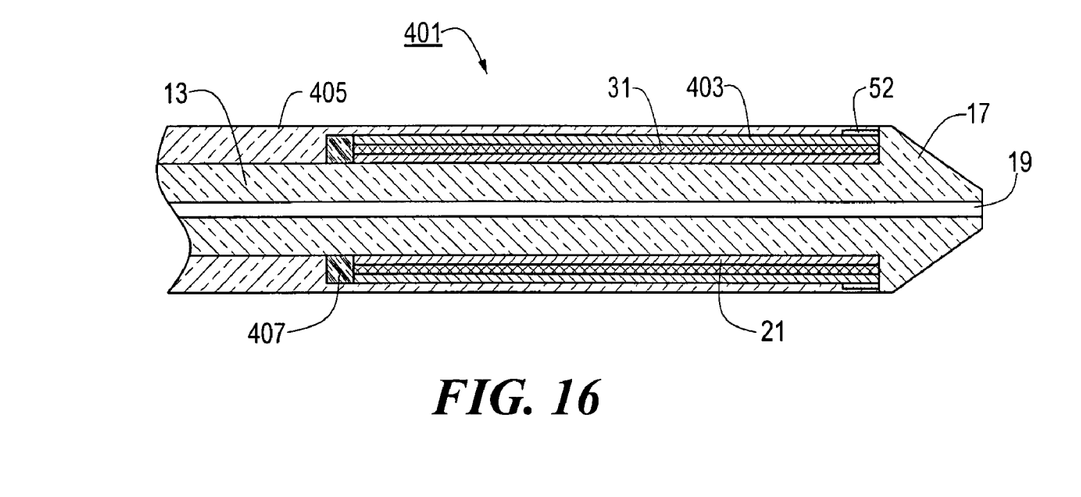
FIG. 16 is a schematic longitudinal section view of a sixth embodiment of a stent delivery system constructed according to the teachings of the present invention.

Referring now to FIG. 16, there is shown a longitudinal section view of a sixth embodiment of a stent delivery system constructed according to the teachings of the present invention, said stent delivery system being represented generally by reference numeral 401.

System 401 is similar in many respects to system 11. One difference between the two systems is that system 401 includes a braided sleeve 403 that, instead of being fabricated directly on top of stent 31 (as in the case of sleeve 41), is separately fabricated and is then slid over stretched stent 31. The inner diameter of sleeve 403 is preferably made to be slightly greater than the outer diameter of stent 31 in a stretched-out state so that sleeve 403 can be easily slid over stretched-out stent 31 while still being capable of retaining stent in said stretched-out state. Another difference between the two system is that system 401 includes a flexible outer catheter 405, catheter 405 being identical to catheter 303. The distal end of catheter 405 is mechanically coupled to the distal end of sleeve 403. Still another difference between the two systems is that system 401 further includes a sleeve holding member 407. Member 407, which is secured to catheter 13, preferably by a friction fit, is adapted to securely receive the proximal end of sleeve 403 in such a way as to prevent sleeve 403 from sliding distally as catheter 405 is advanced over sleeve 403. As can readily be appreciated, catheter 51 of system 401 could be replaced with catheter 51' and jacket 61.

System 401 is used in the same manner as system 11.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A method of manufacturing a stent delivery system, said method comprising the steps of:
    (a) providing an inner catheter;
    (b) compressing a self-expandable stent over said inner catheter;
    (c) while said self-expandable stent is in a compressed state, positioning a braided tube around said inner catheter and said self-expandable stent, said braided tube, when thus positioned around said inner catheter and said self-expandable stent, being adapted for axial movement relative to said self-expandable stent and being dimensioned to maintain said self-expandable stent in said compressed state; and
    (d) positioning an outer catheter around said braided tube such that said braided tube is fixedly attached to said outer catheter tube, and said outer catheter being adapted for axial movement relative to said inner catheter.

2. The method as claimed in claim 1 wherein said braided tube positioning step comprises sliding a pre-formed braided tube over said inner catheter and said self-expandable stent.

3. A method of manufacturing a stent delivery system, said method comprising the steps of:
    (a) providing an inner catheter;
    (b) compressing a self-expandable stent over said inner catheter;
    (c) while said self-expandable stent is in a compressed state, positioning a braided tube around said inner catheter and said self-expandable stent, said braided tube being dimensioned to maintain said self-expandable stent in said compressed state; and
    (d) positioning an outer catheter around said braided tube, said outer catheter being adapted for axial movement relative to said inner catheter, wherein said braided tube positioning step comprises forming a braided tube over said self-expandable stent and said inner catheter.

4. The method as claimed in claim 3 further comprising mechanically coupling said outer catheter to said braided tube for axial movement.

5. The method as claimed in claim 4 wherein said inner catheter and said self-expandable stent are coaxially disposed, wherein said self-expandable stent is flexible in both the longitudinal and radial axes and wherein said compressing step comprises stretching said self-expandable stent longitudinally.

6. The method as claimed in claim 5 wherein said outer catheter is provided with a longitudinal slit extending at least a part of the length thereof, said method further comprising, after said outer catheter positioning step, the step of sealing said longitudinal slit.

7. A method of manufacturing a stent delivery system, said method comprising the steps of:
(a) providing an inner catheter;
(b) compressing a self-expandable stent over said inner catheter;
(c) while said self-expandable stent is in a compressed state, positioning a braided tube around said inner catheter and said self-expandable stent, said braided tube being dimensioned to maintain said self-expandable stent in said compressed state;
(d) positioning an outer catheter around said braided tube, said outer catheter being adapted for axial movement relative to said inner catheter, wherein said braided tube positioning step comprises sliding a pre-formed braided tube over said inner catheter and said self-expandable stent; and
(e) mechanically coupling said outer catheter to said braided tube for axial movement.

8. The method as claimed in claim 7 wherein said inner catheter and said self-expandable stent are coaxially disposed, wherein said self-expandable stent is flexible in both the longitudinal and radial axes and wherein said compressing step comprises stretching said self-expandable stent longitudinally.

9. The method as claimed in claim 8 further comprising, before said compressing step, the step of fixing a stent engaging sleeve to said inner catheter, said self-expandable stent surrounding said stent engaging sleeve, said stent engaging sleeve having an outer surface adapted to engage said self-expandable stent in such a way as to deter said self-expandable stent from sliding proximally relative thereto.

* * * * *